US008802035B2

(12) United States Patent
Jenkins et al.

(10) Patent No.: US 8,802,035 B2
(45) Date of Patent: Aug. 12, 2014

(54) APPARATUS AND METHODS FOR PERFORMING STEPS OF A MULTI-STEP PROCESS IN PARALLEL

(75) Inventors: Kevin Jenkins, Blackstone, MA (US); Paul D. Rainville, Princeton, MA (US); Sylvain Cormier, Ashland, MA (US)

(73) Assignee: Waters Technologies Corporation, Milford, MA (US)

( * ) Notice: Subject to any disclaimer, the term of this patent is extended or adjusted under 35 U.S.C. 154(b) by 884 days.

(21) Appl. No.: 11/917,562

(22) PCT Filed: Jun. 19, 2006

(86) PCT No.: PCT/US2006/023812
§ 371 (c)(1),
(2), (4) Date: May 29, 2008

(87) PCT Pub. No.: WO2007/001984
PCT Pub. Date: Jan. 4, 2007

(65) Prior Publication Data
US 2009/0039024 A1     Feb. 12, 2009

Related U.S. Application Data

(60) Provisional application No. 60/692,684, filed on Jun. 21, 2005.

(51) Int. Cl.
*B01D 15/08* (2006.01)
*G01N 30/04* (2006.01)
*G01N 30/20* (2006.01)
*G01N 30/22* (2006.01)
*B01D 15/18* (2006.01)
*G01N 30/60* (2006.01)

(52) U.S. Cl.
CPC .............. *G01N 30/20* (2013.01); *G01N 30/22* (2013.01); *G01N 2030/202* (2013.01); *B01D 15/1842* (2013.01); *B01D 15/1821* (2013.01); *G01N 30/6047* (2013.01)
USPC .......... 422/540; 422/64; 436/43; 137/625.46; 210/264; 210/198.2

(58) Field of Classification Search
None
See application file for complete search history.

(56) References Cited

U.S. PATENT DOCUMENTS

| 3,373,872 | A | | 3/1968 | Hrdina |
| 4,120,661 | A | | 10/1978 | Naono |
| 4,221,568 | A | * | 9/1980 | Boettger .................... 436/48 |
| 4,614,205 | A | * | 9/1986 | Oroskar .................. 137/625.11 |
| 5,071,547 | A | | 12/1991 | Cazer et al. |
| 5,106,583 | A | | 4/1992 | Raysberg et al. |
| 5,283,036 | A | | 2/1994 | Hofmann et al. |
| 5,630,943 | A | | 5/1997 | Grill |
| 5,695,720 | A | | 12/1997 | Wade et al. |
| 5,950,674 | A | * | 9/1999 | Wylie et al. .................. 137/597 |

(Continued)

FOREIGN PATENT DOCUMENTS

JP          6328676          11/1988

*Primary Examiner* — P. Kathryn Wright
(74) *Attorney, Agent, or Firm* — Muirhead and Saturnelli, LLC

(57) ABSTRACT

Embodiments of the present invention feature a device (1) and method for performing steps of a multi-step process in parallel. The device (1) and method feature a rotor assembly (13) having vessel stations (33) and stator assembly (15) having work positions. The rotor assembly (13) rotates the vessels (17) to the work stations to perform steps of a multi-step process at the same time.

33 Claims, 4 Drawing Sheets

(56) References Cited

U.S. PATENT DOCUMENTS

| | | |
|---|---|---|
| 5,958,227 A | 9/1999 | Uematsu |
| 6,155,123 A | 12/2000 | Bakalyar |
| 6,264,891 B1 | 7/2001 | Heyneker et al. |
| 6,318,157 B1 | 11/2001 | Corso et al. |
| 6,365,105 B1 | 4/2002 | Waters et al. |
| 6,415,670 B1 | 7/2002 | Ohkura et al. |
| 6,453,725 B1 | 9/2002 | Dahlgren et al. |
| 6,491,816 B2 | 12/2002 | Petro |
| 6,979,402 B1 * | 12/2005 | Sprague et al. ............ 210/198.2 |
| 2003/0064007 A1 | 4/2003 | Kim et al. |
| 2004/0094216 A1 * | 5/2004 | Wagner .................. 137/625.46 |

\* cited by examiner

APPARATUS AND METHODS FOR PERFORMING STEPS OF A MULTI-STEP PROCESS IN PARALLEL

CROSS REFERENCE TO RELATED APPLICATIONS

This application claims priority from U.S. Provisional Patent Application No. 60/692,684, filed Jun. 21, 2005. The contents of these applications are incorporated herein by reference.

FIELD OF THE INVENTION

This invention relates to processes and methods having a plurality of steps which processes and methods are performed many times. Embodiments of the present invention have particular relevance to chemical separations.

BACKGROUND OF THE INVENTION

Chemical separations are used in industry, research and medicine for purposes of analysis, research, quality control and diagnosis. One type of chemical separation is chromatography. Chromatographic separations use differences in the affinity of compounds to different media to pull one compound from others. For example, food coloring is often sold as a mixture of compounds in water which impart a color to foods and the like to which they are added. If one places a drop of the food coloring on a paper towel, the food dye spreads through the towel. The paper towel acts as a fixed medium through which the food coloring flows. Upon drying, the drop of food coloring will exhibit bands of different colors representing the different compounds. These compounds have separated in a process based on differences in affinity to the fixed media.

Chromatographic separations are routinely performed with gas samples or samples that are made into gases upon analysis or liquid samples which remain liquid. Separations performed on gas samples are known as gas chromatography, sometimes abbreviated as "GC". Chromatographic separations performed with liquid samples are known as liquid chromatography, or simply, "LC".

Liquid chromatography performed under pressure as fluid flows through a fixed media is known as high performance or high pressure liquid chromatography, or simply, "HPLC". HPLC is routinely performed with a substantially closed system in which a sample is injected into the flow of a fluid moving in a conduit. The fluid containing a sample is directed into a column or cartridge containing a fixed media. For the purpose of this application, the terms column and cartridge are interchangeable. A column is a cylindrical form through which fluid can flow. The column contains a fixed medium, usually a packing of particles, or a monolithic porous material around which the fluid flows.

Each compound in the sample exhibits a characteristic affinity to the fixed medium. Compounds with lower affinity to the medium will exit the column ahead of compounds with higher affinity to the media. The presence of the compounds is often detected by a detector such as a mass spectrometer, optical systems, electrochemical systems or other physical-chemical detection means known in the art.

Analytical chemists and medical researchers often are looking for a particular compound, series of compounds or a compound that has not been previous characterized. Such compound may suggest a disease state, or such compound may suggest the presence of a drug or drug metabolyte. Huge numbers of samples are evaluated using chromatographic processes. These processes become standardized and routine.

A typical process may comprise a loading step, an elution step and one or more, often three to four, wash and/or reconditioning steps. As used herein, a loading step refers to a step in which a sample is introduced into a column or cartridge. An elution step refers to a step in which one or more compounds having affinity to the media in a column are compelled to leave the column. Elution is performed by introducing a change in the fluids flowing through the column. Typically, these changes can comprise a change in hydrogen ion concentration (pH), ionic strength, or solvent/solution changes. The elution step is an important step in analytical processes. The elution step is usually associated with a detecting the presence or absence of a compound. Detectors can be expensive and it is desirable to use detectors efficiently. Washing refers to the process of removing materials from the immobilized phase that are not desired. Reconditioning refers to returning the media to a condition for receiving a further sample. Washing and reconditioning steps are not normally associated with meaningful signals from a detector.

The term "step period" refers to the time in which a step is performed. The longest step period of a multi-step process is the largest period of time for any of the steps of the process. The total process time is the sum of all the work periods associated with a process. And, where different steps are being performed at the same time, the total process time will be the number of steps times the longest step period. The term, "in parallel" refers to in the same work period.

It would be desirable to perform different steps of a multi-step process during a single step period, through multiple step periods, to produce a constant flow of sample eluted from the chromatography media to a detector. That is, the detector will receive the fluid from an elution step for substantially each step period.

SUMMARY OF THE INVENTION

Embodiments of the present invention feature methods and apparatus for performing different steps of a multi-step process during a single step period, through multiple step periods. Performing multiple steps during a single step period allows the steps to be staggered such that a final step, or a step associated with data collection can be performed during all step periods. For embodiments of the invention directed to chromatography, the inventions produce a steady flow of sample eluted from the chromatography medium to a detector. The steady flow of sample to a detector maximizes the utilization of the detector.

One embodiment of the present invention features a device for performing a multi-step process. The multi-step process has a first step, and at least one next step in which each step is performed in a step period and the performance of each step in sequence over time is the total process time. The device has a rotor assembly having an axis of rotation, at least one rotor valve surface, a plurality of vessel stations, and rotor positions. Each vessel station has means for holding a vessel and conduit means for placing a vessel in fluid communication. The conduit means has a working inlet for placing fluid in a vessel and a working outlet for taking fluid out of a vessel. The conduit means has a rotor inlet port and rotor exit port on the at least one rotor valve surface for each vessel station. The rotor valve surface is constructed and arranged to rotate with respect to a stator valve surface on the axis of rotation and cooperate with a stator valve surface. The rotor positions comprise at least one non-working position for each vessel station and at least one working position for each step of the process. Each vessel station may assume each work position and each vessel station assumes a work position as other vessel stations assumes a work position. In the non-working position fluid does not flow through the conduit means and the process elements do not act on a vessel. In the working positions, for each working position the conduit means is in communication with a fluid source or the vessel is in position to be acted upon by process elements for performing a step in a process. As used herein, process elements comprise heating, cooling, incubating or other means of reacting compositions in the vessel. The work positions are for performing a step in a process in each vessel at the same time. And, the work positions are for performing all steps in the process in all vessels as the vessels assume each work position as the rotor assembly rotates. The rotor assembly rotates through each work station to perform all the steps of the process at the work stations in one step period and all the steps in at least one vessel during the total process time.

The devices of the present invention are ideally suited for performing chromatographic separations. When the devices are constructed and arranged to perform chromatographic separations, the rotor assembly has a vessel station for each step of the chromatographic separation. These steps comprise loading of the sample, elution and washing or reconditioning of the vessel. The vessels for performing chromatographic separations are preferably selected from the group comprising chromatography columns and cartridges.

Preferably, the rotor assembly has at least two rotor valve surfaces, separated from each other by said vessel stations. One preferred rotor assembly has a first rotor plate, a second rotor plate and a rotor spanning member. The first rotor plate has one rotor valve surface and the second rotor plate has a second rotor valve surface facing in opposite directions. The first rotor plate and the second rotor plate are separated by a rotor spanning member to form the vessel stations. Preferably, each of the rotor valve surfaces has at least one port selected from the group of ports consisting of the rotor inlet port and rotor outlet port for a work station.

Preferably, the device further comprises a stator assembly. The stator assembly rotatably receives the rotor assembly for rotation between the stop position, first position and said at least one additional position. Preferably, in one embodiment of the present invention, the rotor assembly is interchangeable with other rotor assemblies.

Preferably, the stator assembly has at least one stator valve surface for receiving a rotor valve surface in abutting sealed relationship. The stator valve surface has a stator inlet opening capable of fluid communication with each rotor outlet opening as the rotor assembly rotates and assumes each of the working positions. And, the stator valve surface has a stator outlet opening capable of fluid communication with each rotor inlet opening as the rotor assembly rotates and assumes each of the working positions to allow steps of the multi-step process to be performed in parallel. In the non-working position, the stator inlet opening and the rotor outlet opening, and the stator outlet opening and the rotor inlet opening are out of communication to allow the vessel stations to move without fluid flow.

Preferably, the rotor assembly has two rotor valve surfaces, separated from each other by the vessel stations, and the stator assembly has at least two stator valve surfaces. The rotor assembly is received in the stator assembly between the stator valve surfaces for rotation about the axis.

Preferably, the stator assembly has two stator platforms and a stator spanning member. Each of the two stator platforms has one stator valve surface and each of the stator platforms is held is a spaced position to hold a rotor assembly by a stator spanning member. Preferably, the stator assembly has compression means to apply sealing forces on the stator valve surfaces and the rotor valve surfaces.

Preferably, the device has a motor for powering the rotation of the rotor assembly with respect to the stator assembly. And, preferably, the device has control means and at least one position sensor. The position sensor is capable of determining the position of the rotor assembly with respect to the stator assembly and sending a signal indicative of the position to the control means. The control means is preferably a computer or timing element. Preferably, the control means is capable of receiving instructions from the user and sending command signals to the motor means to move vessel stations to work positions for performing steps of a multi-step process. Preferably, the period of time for the device to stay in a work position corresponds to the duration of the longest step.

Preferably, device has at least one fluid source in communication with the stator outlet openings in the stator valve surface. At least one stator valve inlet is in communication with a detector. The detector receives fluid from a work vessel at a work position, and provides a signal in response to one or more compositions present in the fluid.

Preferably, the device has a seal interposed between or as part of at least one of the rotor valve surface or the stator valve surface. The seal has seal openings for communication with at least one group of opening in the stator valve surface and the rotor valve surface. Preferably, one or more of the seal openings extend on an arc corresponding to the rotation of the rotor valve surface to minimize the time period of a non-working position. Non-working periods can give rise to increases in pressure if the fluids are being driven by one or more pumps. In the alternative, control means can communicate with pumps via one or more pump command signals to stop or slow the pump as the rotor assembly assumes a non-working position.

Preferably, the seal has one face for receiving a rotor valve surface and one face for receiving a stator valve surface. At least one face of the seal has a ridge extending in a circle and having the seal openings to allow additional compressive force on the area immediately surrounding the openings.

Preferably, the device has a stator assembly further comprising an end cap and a compression assembly. The end cap has the stator valve surface and is in communication with one or more fluid sources. The end cap is received in the compression assembly and the compression assembly compressing the stator valve surface, seal and rotor valve surface in sealed engagement. Preferably, compression assembly receives two end caps with facing stator valve surfaces, and receives a rotor assembly with two rotor valve surfaces there between. The end caps facilitate servicing and changing rotor assemblies.

The rotor assemblies can be provided as pre-configured assemblies or can be configured by the end user for his or her particular needs. Vessel stations which are not needed for a particular method can be temporarily or permanently plugged, in which work stations encountering such plugged vessel station will have a non-working period.

Embodiments of the present invention are directed to methods of performing multi-step processes in parallel. One method having features of the present invention had the following steps. The first step is providing a device having a rotor assembly and a stator assembly. The rotor assembly has an axis of rotation, at least one rotor valve surface and a plurality of vessel stations. Each vessel station has conduit means having a working inlet for placing fluid in a vessel and a working outlet for taking fluid out of a vessel. The conduit means has a rotor inlet port and rotor exit port on the rotor valve surface for each vessel station. The rotor valve surface is constructed and arranged to rotate with respect to a stator valve surface on the axis of rotation. The stator assembly receives the rotor assembly for rotation between one or more non-working positions and a plurality of working positions. The stator assembly has at least one stator valve surface for receiving the rotor valve surface in sealed relationship. The rotor valve surface and the stator valve surface cooperate to define at least one non-working and one working position for each work station. In a non-working position the vessel is not be in position to be acted upon by process elements or receiving fluid through the conduit means. In a working position, the conduit means is in communication with a first fluid source for performing a first step in a process and/or the vessel is in position to be acted on by process elements. And, the work stations are constructed and arranged such that each working vessel is capable of assuming each working position and each non-working position as the rotor assembly is rotated with respect to the stator assembly. The work stations are constructed and arranged for performing all the steps of a process during one working time period and at least all the steps of the process in the total time period in one work vessel.

The present method is ideally suited to perform multi-step chromatographic process which often comprise a loading step, an elution step and several washing or reconditioning steps. These steps are assigned to a work station and the rotor assembly rotates a work vessel to perform the steps in the desired sequence. The work vessels are constructed and arranged to perform each step of the process in a staggered manner to allow at least one work vessel to be in communication with a detector to allow steps of the multi-step process to be performed in parallel during a time period. Thus embodiments of the present invention maximize the use of expense detector components.

These and other features and advantages will be apparent upon reviewing the drawings and studying the detailed description that follow.

DETAILED DESCRIPTION OF THE INVENTION

Embodiments of the present invention will be described with respect to the Figures that depict preferred features of the invention as applied to a multi-step chromatography process. Those skilled in the art will readily recognize that the present invention is capable of modification and alteration and performing other processes as well.

Figure 1:
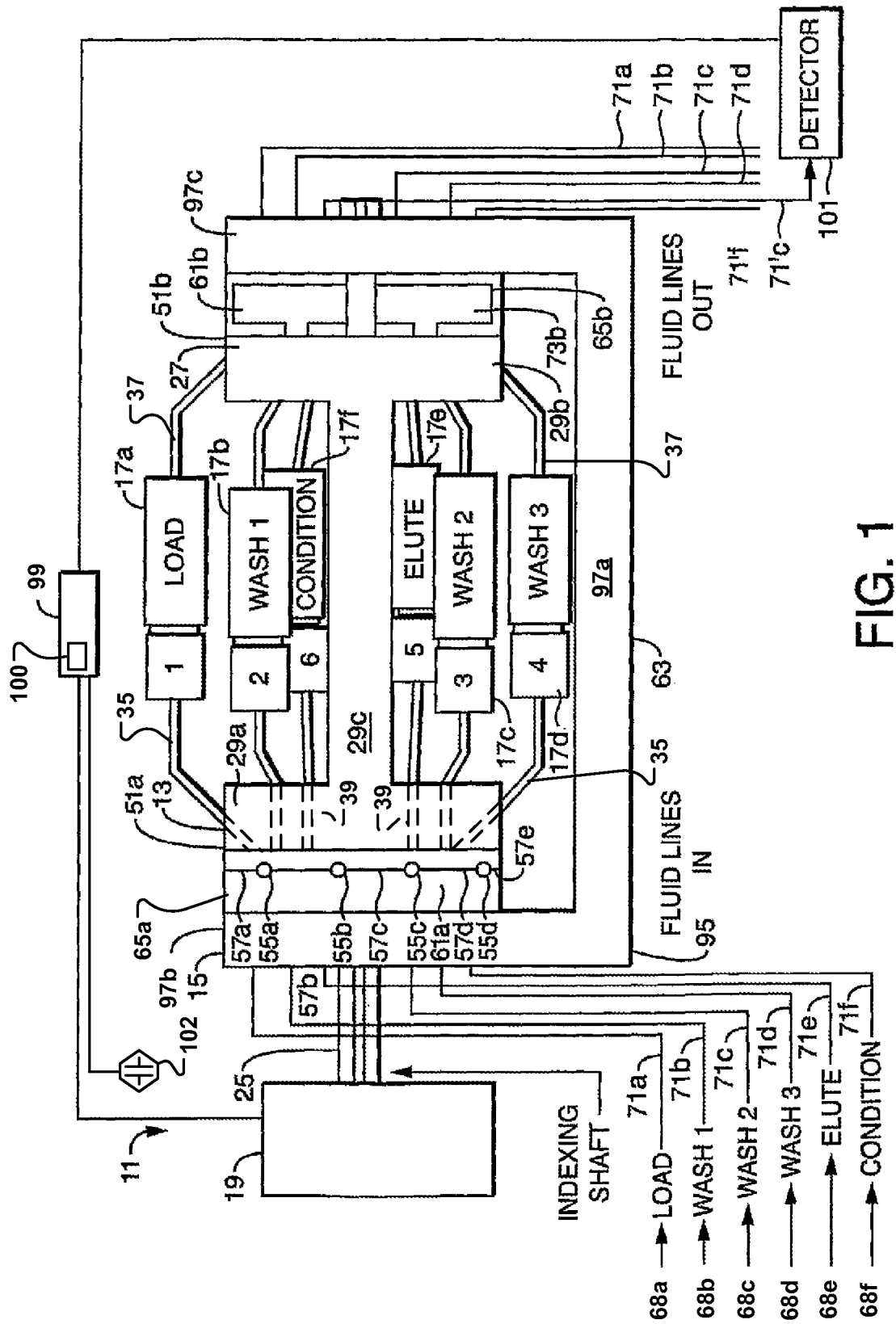
FIG. 1 depicts a schematic view of a device incorporating features of the present invention.

Turning now to FIG. 1, a device, for performing a multi-step process, generally designated by the numeral 11, is depicted. The device 11 has the following major elements: a rotor assembly 13, a stator assembly 15, work vessels 17 *a-f*, motor 19, and control means 99 (e.g., a computer). The device 11 will be described with respect to a multi-step chromatography process having six steps, loading, a first wash, second wash, third wash, eluting, and fourth wash/recondition step. Each step is performed in a step period and the performance of each step in sequence over time is the total process time. For the purpose of this discussion, the elution step will be the longest step and the device will perform all steps in the longest step period to perform the entire process in one total process time. For other processes, the longest step may comprise a step other than the elution step.

The rotor assembly 13 has an axis of rotation, defined by a shaft 25 to which it is mounted. Shaft 25 is coupled to motor 19 for rotation with respect to the stator assembly 15. Other means for powering the rotation of the rotor assembly 13 with respect to the stator assembly 15 may be used. By way of example, without limitation, the motor 19 can be coupled to the rotor assembly 13 or to the stator assembly 15.

The rotor assembly 13 has a rotor housing 27 having a first rotor plate 29*a*, second rotor plate 29*b* and a rotor spanning member 29*c*. First rotor plate 29*a*, second rotor plate 29*b* and spanning member 29*c* can be separate elements or components that are fixed to each other or can be a single unitary structure. As depicted, the rotor housing 27 is a unitary structure made of a substantially rigid metal or plastic. A plastic comprising poly ether ether ketone (PEEK) is preferred.

Figure 2:
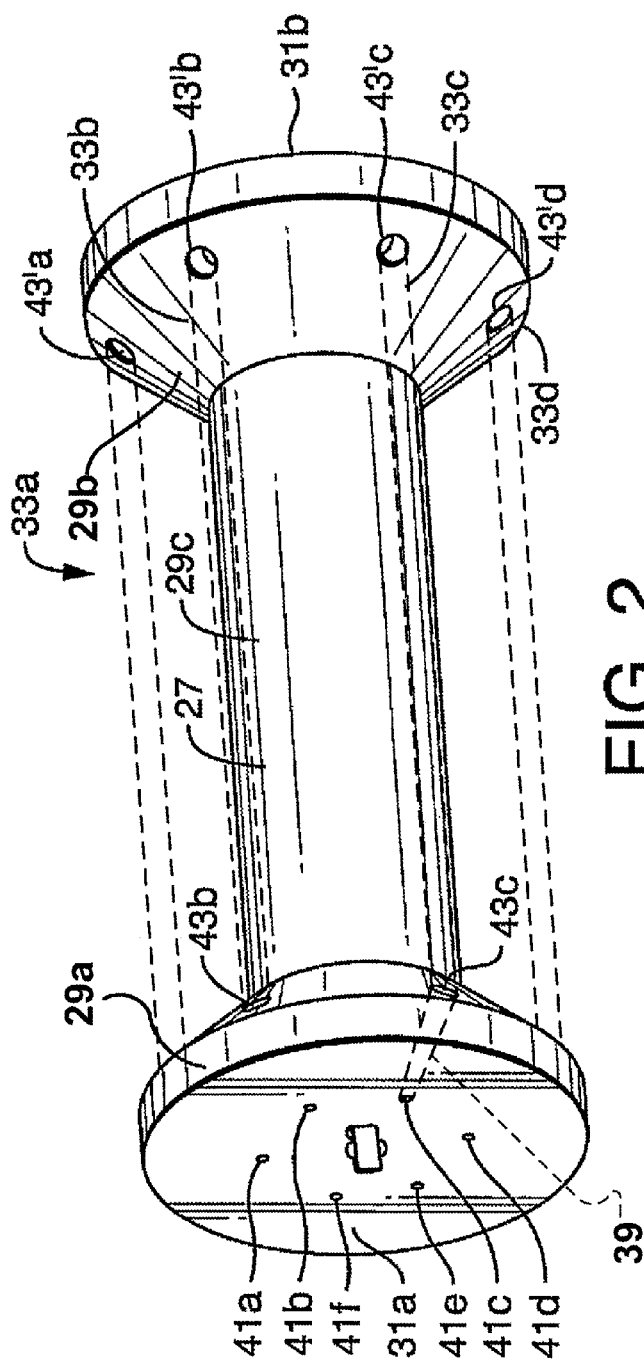
FIG. 2 depicts a rotor assembly having features of the present invention.

Turning now to FIG. 2, first rotor plate 29*a* and second rotor plate 29*b* are sections of the rotor housing 27 having a disk shape. The first rotor plate 29*a* has a rotor valve surface 31*a* having six rotor inlet ports 41*a-f*. The second rotor plate 29*b* has a second rotor valve surface 31*b* facing in an opposite direction, which is not shown but of similar or identical appearance to the first rotor valve surface 31*a*. Second rotor plate 29*b* has rotor outlet ports [not shown] similar to or identical to inlet ports 41*a-f*. Fluid will enter the rotor housing 27 through the inlet ports 41*a-f* and exit the rotor housing 27 through outlet ports [not shown] on the second rotor valve surface 31*b*.

The first rotor plate 29*a* and second rotor plate 29*b* are separated by the rotor spanning member 29*c*. Vessel stations 33*a-f* [of which only a-d are illustrated], spaces for receiving vessels, are denoted with dotted lines in FIG. 2. Vessel stations 33*a-f* are formed in the recess between the rotor plates 29*a* and 29*b*. The vessel stations 33*a-f* are occupied by vessels 17*a-f* in FIG. 1; however, the vessels 17*a-f* may occupy space outside the circumference of the first rotor plate 29*a* and second rotor plate 29*b* with suitable fluid connections. Some of the vessels 17*a-f* would ordinarily be obscured by the spanning member 29*c* and other vessels. FIG. 1 moves the vessels 17 *a-f* from their normal equally spaced positions to allow each vessel 17 *a-f* to be viewed.

Returning now to FIG. 2, the first rotor plate 29*a* and the second rotor plate 29*b* are approximately 5.0 to 10.0 centimeters in diameter and, most preferably, approximately 7.0 to 8.0 centimeters in diameter. The first rotor plate 29*a*, second rotor plate 29*b* and spanning member 29*c* have a combined length of approximately 10.0 to 21.0 centimeters and, most preferably, 14.0 to 18.0 centimeters. Those skilled in the art will recognize that the dimensions are dictated by the length and diameter of the vessels 17*a-f*. The first rotor plate 29*a* and second rotor plate 29*b* have a thickness of approximately 1.0 to 3.0 centimeters.

Each vessel station 33*a-f* has means for holding a vessel 17*a-f* and placing such vessel 17*a-f* in fluid communication with the rotor inlet port 41*a-f* and rotor outlet port [not shown]. Suitable means comprise conduit means in the form of fittings [not shown], known in the art, and inlet tubing 35 and outlet tubing 37. Inlet tubing 35 and outlet tubing 37 provide fluid communication between the work vessel 17*a-f* and rotor inlet ports via passages which form part of the conduit means. One such passage 39 is depicted in hidden lines in FIG. 2. Although only one passage 39 is depicted, a passage 39 is provided for each rotor inlet port 41a-f and each rotor outlet port [not shown].

Passages 39 are formed by potting the tubing into the plastic form as it is made or by drilling the passages 39 after the plastic form is molded. In the alternative, work vessels 17a-f are secured directly to the first rotor plate 29a and second rotor plate 29b by potting. Such work vessels 17a-f would not be normally replaceable and the unit would be used and discarded as a single entity, for user convenience.

Each passage 39 has a working inlet 43a-f, for placing fluid in a work vessel and a working outlet 43'a-f for taking fluid out of a working vessel. In FIG. 1, the working inlets 43a-f and working outlets 43'a-f are occupied by inlet tubing 35 and outlet tubing 37. Each individual passage 39 of first rotor plate 29a communicates with a rotor inlet port 41a-f on the first rotor valve surface 31a. Each individual passage 39 of the second rotor plate 29b communicates with a rotor outlet port on the second rotor valve surface 31b for each vessel station 33a-f.

Turning now to FIG. 1, the first rotor valve surface 31a and the second rotor surface 31b are constructed and arranged to rotate with respect to first stator valve surface 51a and a second stator valve surface 51b on the axis of rotation defined by shaft 25. The first rotor surface 31a, second rotor surface 31b, first stator surface 51a and second stator surface 51b cooperate to form rotor positions comprising at least one non-working position 55a-f [denoted by circles on the end cap 15, of which only 55a-d can be seen]. These non-working positions 55a-f would normally be spaced evenly around the end cap 15 but are clustered for purposes of illustration.

The first rotor valve surface 31a, second rotor valve surface 31b, first stator valve surface 51a and second stator valve surface 51b cooperate to form rotor positions comprising at least one working position 57a-f [denoted by lines on the end cap 15, of which only 57a-d can be seen]. These working positions 57a-f would normally be spaced evenly around the end cap 15 but are clustered for purposes of illustration. Each vessel station 33a-f has at least one working position 57a-f and one non-working position 55a-f for each step of said process.

Turning now to FIG. 1, each vessel station 33a-f may assume each work position 57a-f and each vessel station 33a-f assumes a work position 57a-f as other vessel stations 33a-f assumes a work position 57a-f. And, in a non-working position 55a-f fluid does not flow through passages 39 and process elements do not act on work vessel 17a-f mounted in the vessel station 33a-f. As used herein, the term "process elements" is used to mean apparatus for performing a step in the process other than the movement of fluid. For example, without limitation, process elements comprise apparatus [not shown] for heating, cooling or incubating the contents of a work vessel 17a-f. Such process elements are well known in the art.

For each working position 57a-f passages 39 are in communication with a fluid source to the work vessel 17a-f or the work vessel 17a-f is in position to be acted upon by process elements for performing a step in a process. Each work position 57a-f performs a step in a process in a work vessel 17a-f. And, all the work positions perform all the steps in the process in all work vessels 17a-f as the work vessels 17a-f assume each work position 57a-f as the rotor assembly 13 rotates.

As depicted in FIG. 1, the rotor assembly 13 has a vessel station 33a-f for each step of a multi-step process wherein the multi-step process is a chromatographic separation. The vessels 17a-f are selected from the group comprising chromatography columns and cartridges. For the purpose of this discussion, the steps are arranged with the vessel stations 33a-f sequentially; however, where the device 11 is constructed and arranged to perform a process more than once upon rotation, the work vessels do not need to move sequentially.

A typical chromatography separation process has at least one loading step, at least one wash step and one elution step. As depicted, the work position 57a corresponds to a loading step, the work position 57b through d corresponds to three washing steps, the work position 57e correspond to an elution step, and work position 33f corresponds to a final wash/reconditioning step. As depicted, vessel 17a is in work position 57a. Upon rotation, vessel 17a will assume work position 57b to perform the next step in the process, then 57c, 57d, 57e and finally 57f to perform all the steps in the process. Vessel 17b will be one step behind vessel 17a, and each subsequent vessel 17c-f will be one step further behind. Thus, after an initial period in which each of vessels 17a-f performs the initial step, all the steps of the process are performed in parallel. Each step is staggered among the vessels 17a-f to allow one vessel 17a-f to complete the entire process with each movement of the rotor assembly 13.

As depicted, the rotor assembly has at two rotor valve surfaces 31a and 31b, spaced from each other by the vessel stations 33a-f. Each of the rotor valve surfaces 31a and 31b has at least one port selected from the group of ports consisting of the rotor inlet ports 41a-f and rotor outlet ports. However, those skilled in the art will recognize that the present invention can be implemented with one rotor valve surface in which the conduits extend up to through the spanning member. Or, in a further alternative, the device can have a flatter profile and the vessels 17a-f disposed in a plane with a rotor valve surface 31. The inlet ports 41a-f can be carried on rotor valve 31a and outlet ports can be carried on one rotor valve surface 31b as depicted or reversed or alternated. However, it is preferred to maintain flow in a column or cartridge in a single direction.

The stator assembly 15 rotatably receives the rotor assembly 13 for rotation between the working and non-working positions. Where the work stations are evenly positioned around the stator assembly 15, the rotor assembly 13 can rotate in a mechanical clocklike manner. However, it is preferred to equip the shaft 25 and/or the rotor assembly 13 with position detectors and control means 99. Control means 99 is used in the sense of computers and computer controls. The control means 99 monitors and issues commands to pumps [not shown], valves [not shown] and other components that work in cooperation with the device 11. Preferably, the control means 99 directs the pumps to cease pumping during the periods in which the rotor assembly 13 assumes a non-working position 55a-f. Control means 99 may also have timing elements 100 directing the rotation of rotor assembly 13. In the alternative, control means may receive signals from a detector 101. The detector 101 sends one or more signals indicative of the completion of the process in one vessel 17a-f. Upon the completion of the process, the control means directs the rotation of the rotor assembly 13.

Preferably, the device 11 has a stator assembly 15 as depicted in FIG. 1. Stator assembly 15 has a first end cap 61a, a second end cap 61b and a compression assembly 63. First end cap 61a has one face comprising stator valve surface 51a and second end cap 61b has stator valve surface 51b for receiving rotor valve surface 31a and 31b, respectively in sealed relationship.

Figure 4:
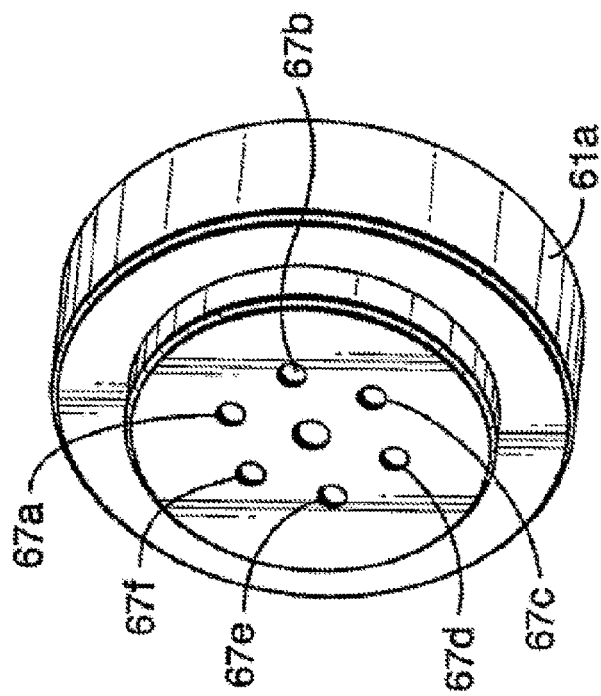
FIG. 4 depicts a back view of an end cap having feature of the present invention.
Figure 3:
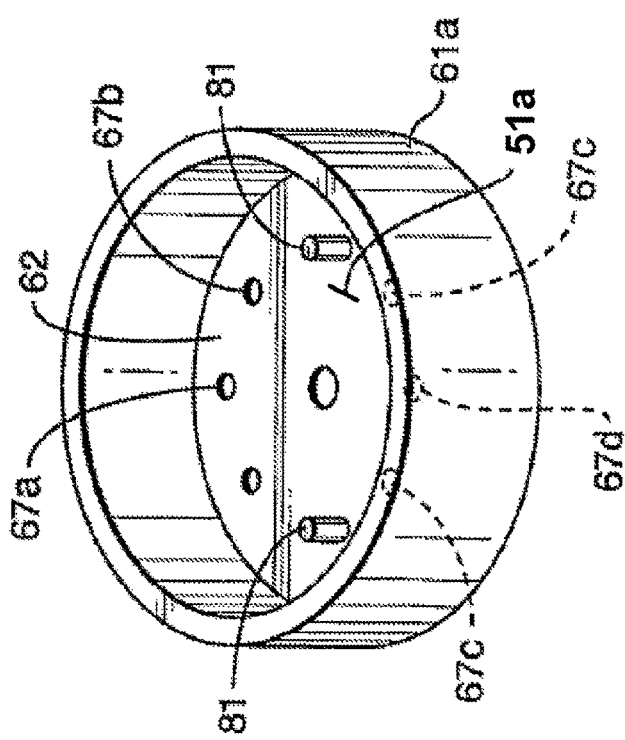
FIG. 3 depicts a front view of an end cap having features of the present invention.

Turning now to FIG. 3, a front view of first end cap 61*a* is depicted. The first end cap 61*a* has stator valve surface 51*a* in a recessed hollow 62. The stator valve surface 51*a* has stator outlet ports 67*a-f*. Second end cap 61*b* has an identical structure with stator valve surface 51*b* of second end cap 61*b* having stator valve inlet ports. FIG. 4 depicts a bottom view of first end cap 61*a*. First end cap 61*a* has a circular projection 79 which fits a circular recess [not shown] in the compression assembly 63.

Turning now to FIG. 1, the outlet ports 67*a-f* have stator passages [not shown] in communication with one or more fluid sources 68*a-f*. Preferably, the first end cap 61*a* and second end cap 61*b* are molded of a plastic material such as PEEK. The passages may comprise one or more tubes 71*a-f* that are secured by potting, gluing or welding into first end cap 61*a* and, similarly, tubes 71'*a-f* into second end cap 61*b*.

The first end cap 61*a*, second end cap 61*b* and the rotor assembly 13 can be bundled into a kit for the convenience of the end-user.

Preferably, as depicted in FIG. 4, the end caps 61*a* and 61*b* have a seal cavities 65*a* and 65*b* for receiving and holding a seal 73*a* and 73*b*. A first seal 73*a* and a second seal 73*b* are interposed between the rotor valve surface 31*a* and stator valve surface 51*a*; and rotor valve surface 31*b* and stator valve surface 51*b* respectively. Preferably, the first seal 73*a* and the second seal 73*b* are affixed to one of the surfaces selected from the group of first and second stator valve surfaces 51*a* and 51*b* and first and second rotor valve surfaces 31*a* and 31*b*.

Figure 6:
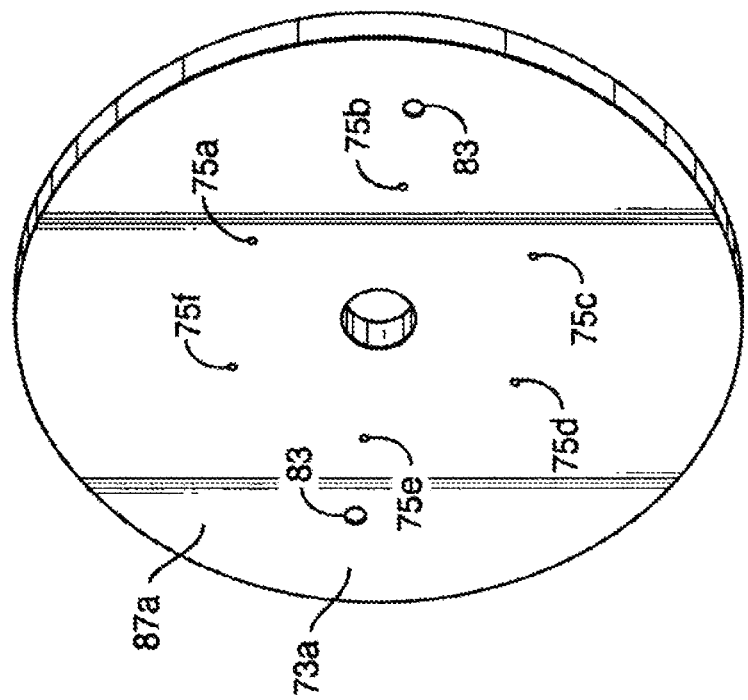

The first seal 73*a* (FIG. 4) is affixed to the first stator valve surface 51*a* in the seal cavity 65*a*. The second seal 73*b* is similarly affixed in a second seal cavity 65*b* in the second end cap 61*b*. Preferably, the first end cap 61*a* and second end cap 61*b* having seal locking means for holding the seal 73*a* and seal 73*b* in the seal cavity 65*a* and 65*b* respectively. The locking means may take many forms including, as depicted in FIGS. 3 and 6, one or more pins 81 which are received in cooperating pin holes 83 in the back side of first seal 73*a* and similarly, the second seal 73*b* (FIG. 1) or adhesive, welding or the like.

Figure 5:
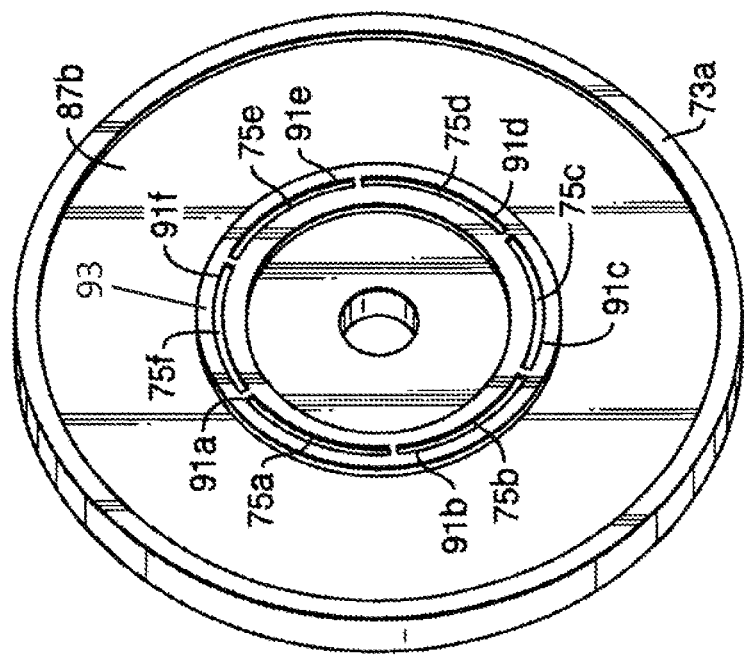
FIG. 5 depicts the front of a seal having features of the present invention; and, FIG. 6 depicts the back of a seal having features of the present invention.

The first seal 73*a* and the second seal 73*b* are made of any flexible resilient material. A siliconized rubber material is preferred. Turning now to FIGS. 5 and 6, the first seal 73*a* and the second seal 73*b* have a first face 87*a* and a second face 87*b*. The first face 87*a* is fitted to a first end cap 61*a* or second end cap 61*b*. The second face 87*b* is, turning now to FIG. 5, constructed and arranged to be received on the rotor valve surface 31*a* or 31*b*. Thus, the rotor valve surfaces 31*a* and 31*b* bear against the seals 73*a* and 73*b*.

The first seal 73*a* and the second seal 73*b* have seal openings 75*a-f* for communication with in let and outlet ports in the first and second stator valve surface 51*a* and 51*b* and the first and second rotor valve surface 31*a* and 31*b*.

The fluid openings 75*a-f* on the second face 87*b* have a extended passage 91*a-f* extending on an arc corresponding to the rotation of the rotor valve surface 31*a* or 31*b* to minimize the time period of a stop position. The each extended passage 91*a-f* forms part of the fluid circuit when pressed against the rotor valve surface 31*a* or 31*b*. The distance between adjacent extended passages 91*a-f* is preferably the diameter of the rotor inlet port 45*a-f* or rotor outlet port 47*a-f* on which the seal 73*a* or 73*b* is pressed against. The extended passages 91*a-f* are on an elevated surface 93 which concentrates the compression forces for sealing the area.

The compression assembly 63 has a "C" shaped clamping frame 95 having a frame spanning member 97*a* and a first arm 97*b* and a second arm 97*c*. The frame 95 is preferably made of plastic or metal. The first end cap 61*a* and the second end cap 61*b* are received in the compression assembly 63, with the rotor assembly 13 and seals 73. The compression assembly 63 compresses the end caps 61*a* and 61*b*, seals 73 and rotor valve surfaces 31*a* and 31*b* in sealed engagement. The clamping frame 95 is made substantially rigid and sized with a span 97*a* between arms 97*a* and 97*b*, smaller than the size of the end caps 61*a* and 61*b*, seals 73 and rotor valve surfaces 31*a* and 31*b*.

Preferably the seals 73 provide sufficient resiliency to allow the end caps 61*a* and 61*b*, seals 73 and rotor valve surfaces 31*a* and 31*b* to be pushed into position. The shaft 25 is inserted into axle openings in the end caps 61*a* and 61*b*, seals 73 and rotor valve surfaces 31*a* and 31*b* locking the components into place. In the alternative, the spanning member 29*c* of the rotor assembly 13 may have adjustment means in the form of screw and nut sections [not shown] allowing the spanning member 29*c* to expand. Or, in the further alternative, the clamping frame 95 is provided with a vice like mechanism [not shown] for reducing the distance between the arms 97*b* and 97*c*.

With the rotor assembly 13 placed in the stator assembly 15, stator valve surfaces 51*a* and 51*b* has stator outlet ports 67*a-f* and stator valve inlet ports 69*a-f* capable of fluid communication with each rotor outlet ports 45*a-f* and rotor inlet ports 47*a-f* as said rotor assembly 13 rotates and assumes each of said working positions. In the non-working position, the stator outlet ports 67*a-f* and stator valve inlet ports 69*a-f* are out of communication to allow vessel stations have a period of time without fluid flow.

The device 11 has a motor 19 for powering the rotation of the rotor assembly 13 with respect to the stator assembly 15. Preferably, the device 11 has at least one position sensor 102 for determining the position of said rotor assembly 13 with respect to a stator assembly 15. The position sensor 102 may take several forms known in the art. For example, without limitation, position sensors known in the art comprise optical sensors, magnetic sensors, stepper motors or mechanical stops.

A preferred position sensor is capable of determining the position of the rotor assembly with respect to the stator assembly and sending a signal indicative of the position to control means 99. Control means 99 comprise, by way of example, without limitation, computers and CPUs having software or firmware capable of receiving and processing signals or timing elements. The control means 99 is capable of receiving instructions and sending command signals to the motor 19 to move vessel 17 to work positions 57*a-f* for performing steps of a multi-step process.

In the alternative, control means 99 is a timing element of a mechanical or electromechanical nature. The timing element 99 is constructed and arranged to send command signals to the motor 19 to move the rotor assembly 13 at interval corresponding to the longest step.

As depicted in FIG. 1, a preferred device 11 has fluid sources, represented by arrows, in communication with the stator outlet ports 67*a-f* in the first stator valve surface 51*a*. Stator inlet ports 69*a-f* are in communication with one or more waste receptacles [not shown] and one detector 101. Preferably, one vessel 17 is in communication with the detector 101 during each time period. That is, the detector 101 receives fluid associated with the sample associated with an elution step during each time period. Detectors 101 are expensive and it is desirable to maximize the input of fluid being analyzed and minimize fluid associated with washes and reconditioning. A preferred detector is a mass spectrometer. The detector 101 provides a signal in response to one or more compositions present in the fluid. This signal is preferably received an stored in a information processing system [not shown] known in the art.

The method of the present invention is described with respect to the operation of an embodiment of the invention. The method is directed to performing steps in a multi-step process in parallel. In operation, a device 11 is provided to the user. The device 11 has a rotor assembly 13 and a stator assembly 15. The rotor assembly 13 has an axis of rotation corresponding generally with the shaft 25. The rotor assemble 13 has two rotor valve surfaces 31a and 31b and a plurality of vessel stations 33a-f. Each vessel station 33a-f has conduit means in the form of tubing 35 and passages 39 having a working inlet 43a-f for placing fluid in a vessel 17a-f and a working outlet 43'a-f for taking fluid out of a vessel 17a-f. Each passages 39 has a rotor inlet port 41a-g and rotor outlet port on the one rotor valve surfaces 31a and 31b. The rotor valve surfaces 31a and 31b are constructed and arranged to rotate with respect to stator valve surface 51a and 51b.

If the rotor assembly 13 and stator assembly 15 are not pre-assembled, the user places the rotor assembly 13 in the stator assembly 15. The stator assembly 15 receives the rotor assembly 13 for relative rotation to work positions and non-working positions. As depicted in FIG. 1, a first vessel 17a is in a first working position. This first working position, for the purpose of this discussion, is a loading step. In this first working position, the vessel 17a receives a fluid containing a sample. The fluid is introduced through passages 39 and tubing 35. The rotor inlet port 41a (FIG. 2) is in communication with stator outlet port 67a (FIG. 3) to allow fluid to enter the vessel 17a. The rotor outlet port 67a is in fluid communication with stator inlet port to allow fluid to exit the vessel 17a. In a similar manner each vessel 17b-f receives fluid for a step of the process including fluids for the steps of washing (of which three are described), eluting and washing reconditioning.

After a first the period of time, the vessel 17a is rotated to the next position. And, a new vessel 17b assumes the position formerly occupied by vessel 17a. In a similar manner each of the vessels 17c-f advance to the next work position 57. As the vessels 17a-f advance to the next work position 57 a-f, each vessel passes a non-working position 55a-f. In a working position the passages 39 and tubing 35 are in communication with a fluid source for performing a first step in a process in the vessels 17a-f. In the non-working position 55, the passages 39 and tubing 35 are not in communication with a fluid source for performing a first step in a process in the vessels 17a-f. The work positions 57 and non-working positions 55 are constructed and arranged to allow each vessel 17a-f to assume a working position with the others and to assume a non-working position with the others, for performing more than one step of a process during one working time period.

Preferably, the device 11 has control means 99 for controlling the movement of the rotor assembly 13 with respect to the stator assembly 15. Preferably, the device 11 has a detector 101. Embodiments of the present method and apparatus maximize the use of detectors by allowing substantially each time period associated with the performance of a process to have sample to flow to the detector.

These and other features and advantages will be apparent to those skilled in the art. The present discussion has described in detail the preferred embodiments of the invention which individuals skilled in the art will readily recognize are capable of alteration and modification. Thus the invention should not be limited to the precise details presented herein but should encompass the subject matter as set forth in the claims that follow and the equivalent apparatus and methods. 25. The method of claim 23 wherein said rotor assembly has a vessel station for each step of said multi-step process.

What is claimed:

1. A device for performing a multi-step process, said multi-step process having a first step and at least one next step, in which each step is performed in a step period and the performance of the steps over time is the total process time, said device for performing the steps in parallel, the device comprising:

a rotor assembly including two rotor valve surfaces, and a plurality of vessel stations;

each vessel station having at least one conduit, said conduit having a working inlet for placing fluid in a work vessel at the vessel station and a working outlet for taking fluid out of a working vessel at the vessel station, said conduit having a rotor inlet port on a first of the two rotor valve surfaces and rotor outlet port on a second of said two rotor valve surfaces for each vessel station;

a stator assembly including two stator valve surfaces and two end caps, wherein each of said two end caps includes a recessed cavity having an inner surface whereby the inner surface of said each end cap is one of the two stator valve surfaces, said stator assembly rotatably receiving said rotor assembly for rotation between a plurality of rotor positions, said rotor positions comprising at least one non-working position for each vessel station and at least one working position for each step of said process; and two seals, wherein each of said two seals is affixed in the recessed cavity of one of the two end caps and is disposed between one of the two rotor valve surfaces and one of said two stator valve surfaces of said one end cap, each of said two seals being formed from a flexible resilient material and having seal openings for fluid communication between said one stator valve surface and said one rotor valve surface, said seal openings of each of said two seals including extended passages formed on only a first face of said each seal, wherein the extended passages formed on only the first face extend on an arc corresponding to the rotation of the rotor valve surface to limit the time period of the at least one non-working position, wherein, for each of said two seals, an elevated surface of said each seal is elevated with respect to a surface of the first face of said each seal and wherein the extended passages formed on the first face are formed in the elevated surface of said each seal which concentrates compressive force on an area immediately surrounding the seal openings, wherein, in said at least one non-working position, each of the two stator valve surfaces is not in fluid communication with the conduit, wherein, in said at least one working position, for each working position, said conduit is in communication with a fluid source via the two seals and the two stator valve surfaces, and wherein said rotor assembly is operable to rotate each of said vessel stations to each work position such that all the steps of said process are performed at each of said vessel stations during the total process time and such that each step in the multi-step process is performed during at least one step period.

2. The device of claim 1 wherein said rotor assembly has a vessel station for each step of said multi-step process.

3. The device of claim 1 wherein said work vessels are selected from the group comprising chromatography columns and cartridges.

4. The device of claim 1, wherein said two rotor valve surfaces are separated from each other by said vessel stations.

5. The device of claim 4, wherein said rotor assembly comprises a first rotor plate, second rotor plate and a rotor spanning member, said first rotor plate having a first of the two rotor valve surfaces and said second rotor plate having a second of the two rotor valve surfaces, said first rotor valve surface and said second rotor valve surface facing in opposite directions, said first rotor plate and second rotor plate separated by said rotor spanning member to form said vessel stations.

6. The device of claim 1 further comprising at least one position sensor for determining the position of said rotor assembly with respect to said stator assembly.

7. The device of claim 1 wherein a first of the two stator valve surfaces has a stator inlet opening capable of fluid communication with each rotor outlet port opening of the second rotor valve surface as said rotor assembly rotates and assumes each of said working positions; and, a second of the stator valve surfaces has a stator outlet opening capable of fluid communication with each rotor inlet port opening of the first rotor valve surface as said rotor assembly rotates and assumes each of said working positions to allow steps of said multi-step process to be performed in parallel.

8. The device of claim 7 wherein said rotor assembly in said non-working position has said stator inlet opening and each rotor outlet port opening and said stator outlet opening and each rotor inlet port opening out of communication to allow said vessel stations to move without fluid flow.

9. The device of claim 7 wherein said two rotor valve surfaces are separated from each other by said vessel stations and said rotor assembly is rotatably received in said stator assembly between said stator valve surfaces.

10. The device of claim 9, wherein said stator assembly comprises a compression assembly to apply sealing forces on said two stator valve surfaces and said two rotor valve surfaces.

11. The device of claim 1 further comprising a motor for powering the rotation of said rotor assembly with respect to said stator assembly.

12. The device of claim 11 further comprising a controller and at least one position sensor, said position sensor capable of determining the position of said stator assembly with respect to said rotor assembly and sending a signal indicative of said position to said controller, said controller capable of receiving instructions and sending command signals to said motor to move vessel stations to work positions for performing steps of a multi-step process.

13. The device of claim 12 wherein said controller has a timing element to set the duration of said rotor assembly in said at least two work positions to a period of time corresponding to the duration of the longest step.

14. The device of claim 11 further comprising at least one fluid source in communication with at least one stator outlet opening in a first of the two stator valve surfaces.

15. The device of claim 11 further comprising at least one detector in communication with at least one stator inlet opening of a first of the two stator valve surfaces for receiving the fluid from at least one work vessel at a work position, said detector providing a signal in response to one or more compositions present in the fluid.

16. The device of claim 1, further comprising a compression assembly compressing the two stator valve surface, said two seals, said two end caps and said two rotor valve surfaces in sealed engagement.

17. The device of claim 1 further comprising a lock for holding said each seal to said one stator valve surface of said one end cap.

18. The device of claim 17 wherein the lock comprises pins.

19. The device of claim 1, wherein said seal openings include circular openings on a second face of said each seal.

20. A method of performing steps in a multi-step process in parallel, comprising:
providing a device having a rotor assembly, a stator assembly, and two seals, said rotor assembly having an axis of rotation, including two rotor valve surfaces and having a plurality of vessel stations, each vessel station having at least one conduit having a working inlet for placing fluid in a work vessel at the vessel station and a working outlet for taking fluid out of a working vessel at the vessel station, said conduit having a rotor inlet port on a first of the two rotor valve surfaces and rotor outlet port on a second of said two rotor valve surfaces for each vessel station, said rotor valve surface constructed and arranged to rotate with respect to the stator assembly on said axis of rotation; and,
said stator assembly including two stator valve surfaces and two end caps, wherein each of said two end caps includes a recessed cavity having an inner surface whereby the inner surface of said each end cap is one of the two stator valve surfaces, said stator assembly rotatably receiving said rotor assembly for rotation between at least three rotor positions comprising at least one non-working position in which fluid does not flow through said conduit, a first working position in which said conduit is in communication with a first fluid source for performing a first step in a process, and at least one further working position in which said conduit is in communication with at least one further fluid source for performing at least one additional step in a process,
said rotor assembly being rotatable, relative to said stator assembly, to place at least one work vessel in a first working position and at least one work vessel in an additional working position during a first working time period,
said rotor assembly being rotatable, relative to said stator assembly, to place at least one work vessel in said non-working position during a non-working period, and
said rotor assembly being rotatable, relative to said stator assembly, such that each working vessel assumes each working position during a total process time period during which each step in the multi-step process is performed, and such that more than one step of the multi-step process is performed during one working time period,
wherein each of the two seals is affixed in the recessed cavity of one of the two end caps and is disposed between one of the two rotor valve surfaces and one of the two stator valve surfaces of said one end cap, each of said two seals being formed from a flexible resilient material and including seal openings for fluid communication between said one stator valve surface and said one rotor valve surface, said seal openings of each of said two seals including extended passages formed on only a first face of said seal, wherein the extended passages formed on only the first face extend on an arc corresponding to the rotation of the rotor valve surface to limit the non-working period, and
wherein, for each of the two seals, an elevated surface of the seal is elevated with respect to a surface of the first face of said each seal and wherein the extended passages formed on the first face are formed in the elevated surface of the said each seal which concentrates compressive force on an area immediately surrounding the seal openings.

21. The method of claim 20 wherein a first of the two stator valve surfaces has a stator inlet opening capable of fluid communication with each rotor outlet port opening of the second rotor valve surface as said rotor assembly rotates and assumes each of said working positions; and, a second of the stator valve surfaces has a stator outlet opening capable of fluid communication with each rotor inlet port opening of the first rotor valve surface as said rotor assembly rotates and assumes each of said working positions to allow steps of said multi-step process to be performed in parallel during a time period.

22. The method of claim 20 wherein said rotor assembly has a vessel station for each step of said multi-step process.

23. The method of claim 20 wherein multi-step process is a chromatographic separation.

24. The method of claim 20 further comprising at least one position sensor for determining the position of said rotor assembly with respect to a stator assembly.

25. The method of claim 20 wherein said rotor assembly in said non-working position has a stator inlet opening of one of the two stator valve surfaces and said rotor outlet port of the second rotor valve surface and a stator outlet opening of a second of the two stator valve surfaces and a rotor inlet port of the first rotor valve surface out of communication to allow said vessel stations to move without fluid flow.

26. The method of claim 20 wherein said two rotor valve surfaces are separated from each other by said vessel stations, said rotor assembly rotatably received in said stator assembly between said stator valve surfaces.

27. The method of claim 20 further comprising a motor for powering the rotation of said rotor assembly with respect to said stator assembly.

28. The method of claim 27 further comprising a controller and at least one position sensor, said position sensor capable of determining the position of said stator assembly with respect to said rotor assembly and sending a signal indicative of said position to said controller, said controller capable of receiving instructions and sending command signals to said motor to move vessel stations to work positions for performing steps of a multi-step process.

29. The method of claim 28 wherein said controller has a timing element to set the duration of said rotor assembly in said at least two work positions to a period of time corresponding to the duration of the longest step.

30. The method of claim 29 wherein said controller is programmed to perform at least one elution step, one wash step and at least one load step in a single time period.

31. The method of claim 20 further comprising at least one detector in communication with at least one stator inlet opening of a first of the two stator valve surfaces for receiving the fluid from at least one work vessel at a work position, said detector providing a signal in response to one or more compositions present in the fluid which signal is indicative of the end of a work period.

32. The method of claim 20, wherein the multi-step process performed using the device is a chromatographic separation which includes a loading step, a plurality of washing steps, an elution step, and a reconditioning step, the rotor assembly includes two rotor plates separated by a rotor spanning member with each of the two rotor plates having a surface that is one of the two rotor valve surfaces, and the plurality of vessel stations are formed in the recess between the two rotor plates and includes a vessel station for each step of the chromatographic separation, and wherein the elution step is a longest step in the multi-step process.

33. The method of claim 32, wherein after an initial period in which each of the steps of the chromatographic separation are performed once, all steps of the multi-step process are performed in parallel.

\* \* \* \* \*